(12) United States Patent
Endo et al.

(10) Patent No.: US 11,696,672 B2
(45) Date of Patent: Jul. 11, 2023

(54) ENDOSCOPIC PUNCTURE NEEDLE

(71) Applicant: Olympus Corporation, Hachioji (JP)

(72) Inventors: Takuo Endo, Sagamihara (JP); Tomofumi Katayama, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 618 days.

(21) Appl. No.: 16/677,776

(22) Filed: Nov. 8, 2019

(65) Prior Publication Data
US 2020/0069154 A1   Mar. 5, 2020

Related U.S. Application Data

(63) Continuation of application No. PCT/JP2017/020691, filed on Jun. 2, 2017.

(51) Int. Cl.
*A61B 1/00* (2006.01)
*A61B 1/018* (2006.01)
(Continued)

(52) U.S. Cl.
CPC .......... *A61B 1/00098* (2013.01); *A61B 1/018* (2013.01); *A61B 17/3478* (2013.01); *A61B 8/12* (2013.01); *A61M 25/09* (2013.01)

(58) Field of Classification Search
CPC . A61B 1/00098; A61B 1/018; A61B 17/3478; A61B 1/0008; A61B 2017/0034;
(Continued)

(56) References Cited

U.S. PATENT DOCUMENTS 6,551,289 B1   4/2003  Higuchi et al.
10,149,665 B2  12/2018  Eckerline et al.
(Continued)

FOREIGN PATENT DOCUMENTS

CN   102626337 A   8/2012
EP      3000422      3/2016
(Continued)

OTHER PUBLICATIONS

Nov. 3, 2021 Office Action issued in Chinese Patent Application No. 201780091400.
(Continued)

*Primary Examiner* — Brooke Labranche
*Assistant Examiner* — Lauren Dubose
(74) *Attorney, Agent, or Firm* — Oliff PLC

(57) ABSTRACT

The disclosed technology is directed to a puncture needle access system for introducing guide wire into an interior of a tubular organ. The puncture needle access system includes an endoscope having an insertion portion. An endoscopic puncture needle is configured to be engaged with the insertion portion and includes an elongated tubular sheath having a lumen that extends in a longitudinal direction through the elongated tubular sheath. A tubular needle tube is inserted movably in the longitudinal direction into the lumen of the elongated tubular sheath. The tubular needle tube includes an inclined cutting-edge face formed at a distal end. The elongated tubular sheath includes an inclined surface oriented toward a distal end of the sheath so that the inclined surface comes closer to the elongated tubular sheath. The distal end of the sheath is located on a proximal end side of the sheath relative to a distal end of the inclined surface.

16 Claims, 12 Drawing Sheets

(51) Int. Cl.
*A61B 17/34* (2006.01)
*A61B 8/12* (2006.01)
*A61M 25/09* (2006.01)

(58) Field of Classification Search
CPC ..... A61B 10/04; A61B 2010/045; A61B 8/12; A61B 17/3417; A61B 10/0233; A61B 17/3403; A61B 17/3496; A61B 2090/08021; A61M 2025/009
See application file for complete search history.

(56) References Cited

U.S. PATENT DOCUMENTS

| | | | | |
|---|---|---|---|---|
| 2010/0030105 | A1* | 2/2010 | Noishiki | A61B 10/025 600/567 |
| 2013/0035639 | A1* | 2/2013 | Clancy | A61B 17/34 604/164.13 |
| 2014/0276051 | A1* | 9/2014 | Hoffman | A61B 17/3417 604/164.09 |
| 2015/0011941 | A1 | 1/2015 | Saeki | |
| 2015/0328435 | A1* | 11/2015 | Mathis | A61B 17/3417 606/41 |

FOREIGN PATENT DOCUMENTS

| | | |
|---|---|---|
| JP | 2001-079088 | 3/2001 |
| JP | 2004-290517 | 10/2004 |
| JP | 2006-288615 | 10/2006 |
| JP | 2010-167287 | 8/2010 |
| JP | 2012-235878 | 12/2012 |
| JP | 2013-172803 | 9/2013 |
| WO | WO-2018025968 A1 * | 2/2018 ..... A61B 17/320016 |

OTHER PUBLICATIONS

International Search Report and Written Opinion from corresponding International Application No. PCT/JP2017/020691, dated Jun. 2, 2017.

* cited by examiner

ENDOSCOPIC PUNCTURE NEEDLE

CROSS-REFERENCE TO RELATED APPLICATION

This application is a continuation application of PCT Application No. PCT/JP 2017/020691 filed on Jun. 2, 2017, which is hereby incorporated by reference in its entirety.

TECHNICAL FIELD

The technology disclosed herein relates generally to endoscope system, and more particularly, some embodiments relate to an endoscopic puncture needle used in a puncture needle access system for introducing guide wire into an interior of a tubular organ that combined with an ultrasonic endoscope.

DESCRIPTION OF THE RELATED ART

Known endoscopic puncture needles include those having an outer tube with an intrinsic bending tendency and a needle with rigidity higher than the outer tube as disclosed in EP 3000422A1.

The endoscopic puncture needle of EP 3000422A1 has an outer tube corrected straight by causing a needle to protrude from a distal end opening of the outer tube. The endoscopic puncture needle is used to puncture a tubular tissue. The outer tube is inserted, at a distal end portion thereof, into a tubular tissue, and the needle is then withdrawn, whereby the outer tube is bent in one direction in the tubular tissue. Subsequently, a guide wire is introduced into the bent outer tube, and is caused to advance along the bent direction of the outer tube in the one direction from the distal end opening of the outer tube toward the tubular tissue.

However, the endoscopic puncture needle of EP 3000422A1 involves an inconvenience that the introducing direction of the guide wire is limited to one direction by the direction of bending of the outer tube to be bent when the needle is withdrawn. In other words, if the bent direction of the outer tube is found to be wrong after the outer tube has been once introduced, the operation needs to be performed again from the puncture work. The use of this endoscopic puncture needle is, therefore, accompanied by inconveniences that the puncture work is laborious and a heavy physical burden is placed on the patient.

BRIEF SUMMARY OF EMBODIMENTS

One aspect of the disclosed technology is directed to a puncture needle access system for introducing guide wire into an interior of a tubular organ. The success system includes an endoscope having an insertion portion. An endoscopic puncture needle is configured to be engaged with the insertion portion. The endoscopic puncture needle includes an elongated tubular sheath having a lumen that extends in a longitudinal direction through the elongated tubular sheath. A tubular needle tube is inserted movably in the longitudinal direction into the lumen of the elongated tubular sheath. The tubular needle tube includes an inclined cutting-edge face formed at a distal end thereof relative to the longitudinal direction. The elongated tubular sheath includes an inclined surface oriented toward a distal end of the sheath so that the inclined surface comes closer to a central axis of the elongated tubular sheath. The distal end of the sheath on a side facing the inclined surface with the lumen interposed in a radial direction therebetween is located on a proximal end side of the sheath relative to a distal end of the inclined surface.

Another aspect of the disclosed technology is directed to an endoscopic puncture needle used in an endoscope having an insertion portion. The endoscopic puncture needle includes an elongated open ended tubular sheath. A tubular needle tube is configured to be inserted movably in a longitudinal direction into the elongated open ended tubular sheath. The tubular needle tube includes an inclined cutting-edge face formed at a distal end thereof relative to the longitudinal direction. The elongated open ended tubular sheath includes an inclined surface oriented toward a distal end of the sheath so that the inclined surface comes closer to a central axis of the elongated tubular sheath. And the distal end of the sheath on a side facing the inclined surface interposed in a radial direction therebetween is located on a proximal end side of the sheath relative to a distal end of the inclined surface.

A further aspect of the disclosed technology is directed to a method of introducing a guide wire into an interior of a tubular organ. The method comprising: inserting an insertion portion of an endoscope into a body; guiding a needle tube and a sheath to advance relative to the insertion portion introduced in the body, whereby the needle tube and sheath are caused to puncture a tubular wall of the tubular organ; retreating the needle tube toward a proximal end side relative to the sheath with the sheath still remaining at a distal end thereof in the interior of the tubular organ; and inserting the guide wire to extend from the distal end of the sheath into the interior of the tubular organ with the needle tube being located at a proximal end side thereof on a distal end relative to the proximal end of the sheath.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

In view of the circumstances described hereinbefore, the disclosed technology has as an object thereof the provision of an endoscopic puncture needle that enables to choose the inserting direction of a guide wire after puncture by a needle.

Regarding an endoscopic puncture needle 1 according to one embodiment of the disclosed technology, a description will hereinafter be made with reference to the drawings.

Figure 1:
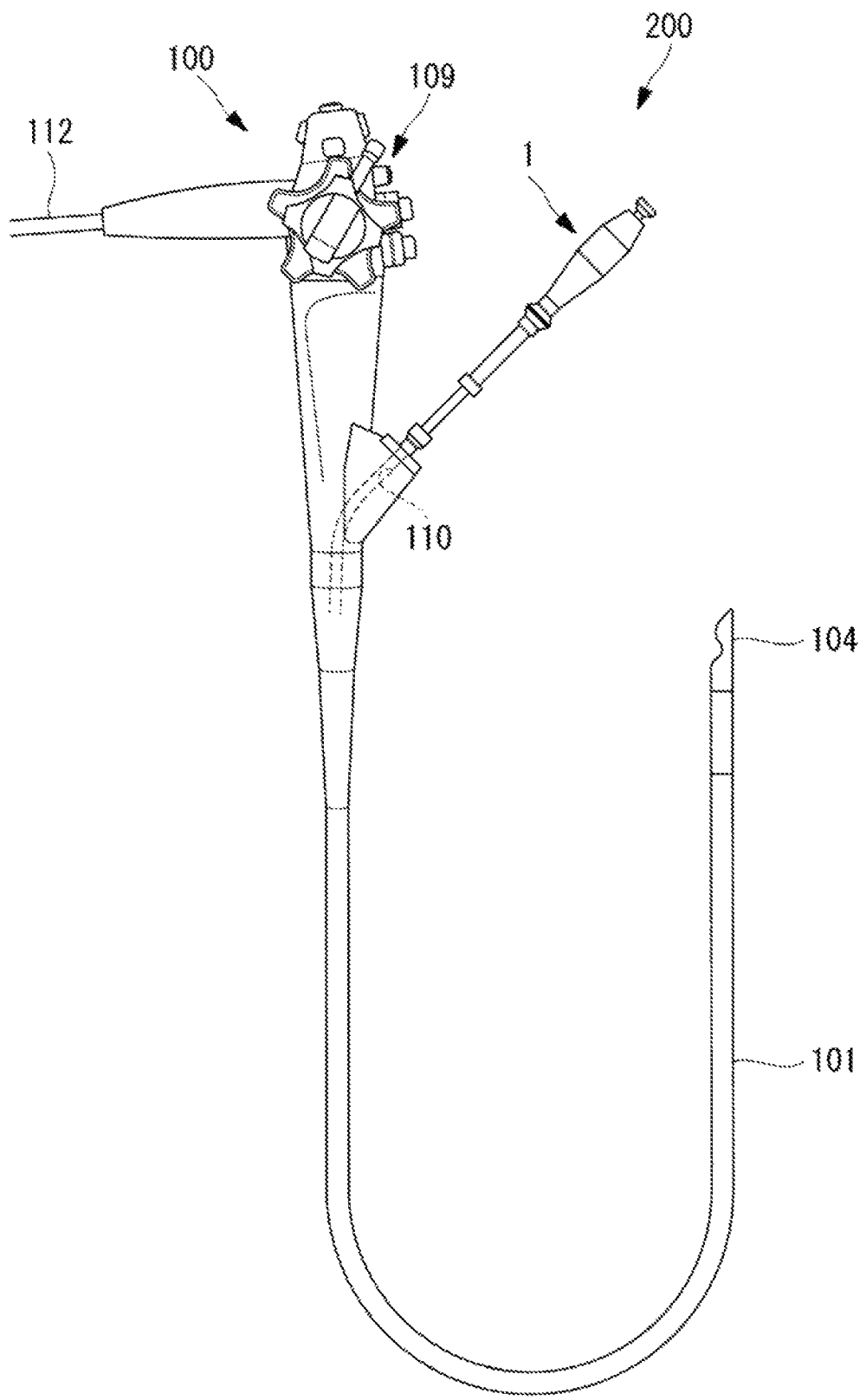
FIG. 1 is a view illustrating an example of a puncture needle access system in which an endoscopic puncture needle according to one embodiment of the disclosed technology is used.

As illustrated in FIG. 1, the endoscopic puncture needle 1 according to this embodiment is for use in a puncture needle access system 200 combined with an ultrasonic endoscope 100.

The ultrasonic endoscope 100 can be applied to perform diagnosis or treatment on the digestive organs or respiratory organs. The ultrasonic endoscope 100 includes an insertion portion 101 to be inserted into the body from a distal end thereof, an operation mechanism 109 attached to a proximal end of the insertion portion 101, a universal cord 112 connected at an end thereof to a side portion of an operation mechanism 109, and an unillustrated ultrasonic observation portion connected to an opposite of the universal cord 112.

The insertion portion 101 includes, at the distal end thereof, an unillustrated optical imaging system configured to perform optical observation, and an ultrasonic probe 104 configured to perform ultrasonic observation.

The optical imaging system includes an imaging optical system with a field of vision directed diagonally forward, and an image sensor, such as a charge coupled device (CCD) or a complementary metal-oxide semiconductor (CMOS), configured to detect an image of an object as entered through the imaging optical system.

The ultrasonic probe 104 includes an unillustrated ultrasonic transducer that emits and receives ultrasonic waves. Described specifically, the ultrasonic transducer emits ultrasonic waves toward an observation target. The ultrasonic waves strike the observation target and are reflected, and the reflected waves are received by the ultrasonic transducer. The ultrasonic probe 104 is configured to output signals to the ultrasonic observation portion based on the reflected waves received by the ultrasonic transducer. The ultrasonic probe 104 in this embodiment is used to acquire an ultrasonic wave image of a tissue as an access target, and also to acquire an ultrasonic wave image of a needle tube 6 (see FIG. 4) in the course of procedures of access for introducing guide wire into an interior of a tubular organ. The needle tube 6 will be described hereinafter.

The insertion portion 101 includes a channel 110 that extends in a longitudinal direction through the insertion portion 101. The channel 110 opens, at one end thereof, in a vicinity of the distal end of the insertion portion 101, and at an opposite end thereof, opens in a side wall of the ultrasonic endoscope 100, the side wall being located in a vicinity of the operation mechanism 109.

Figure 2:
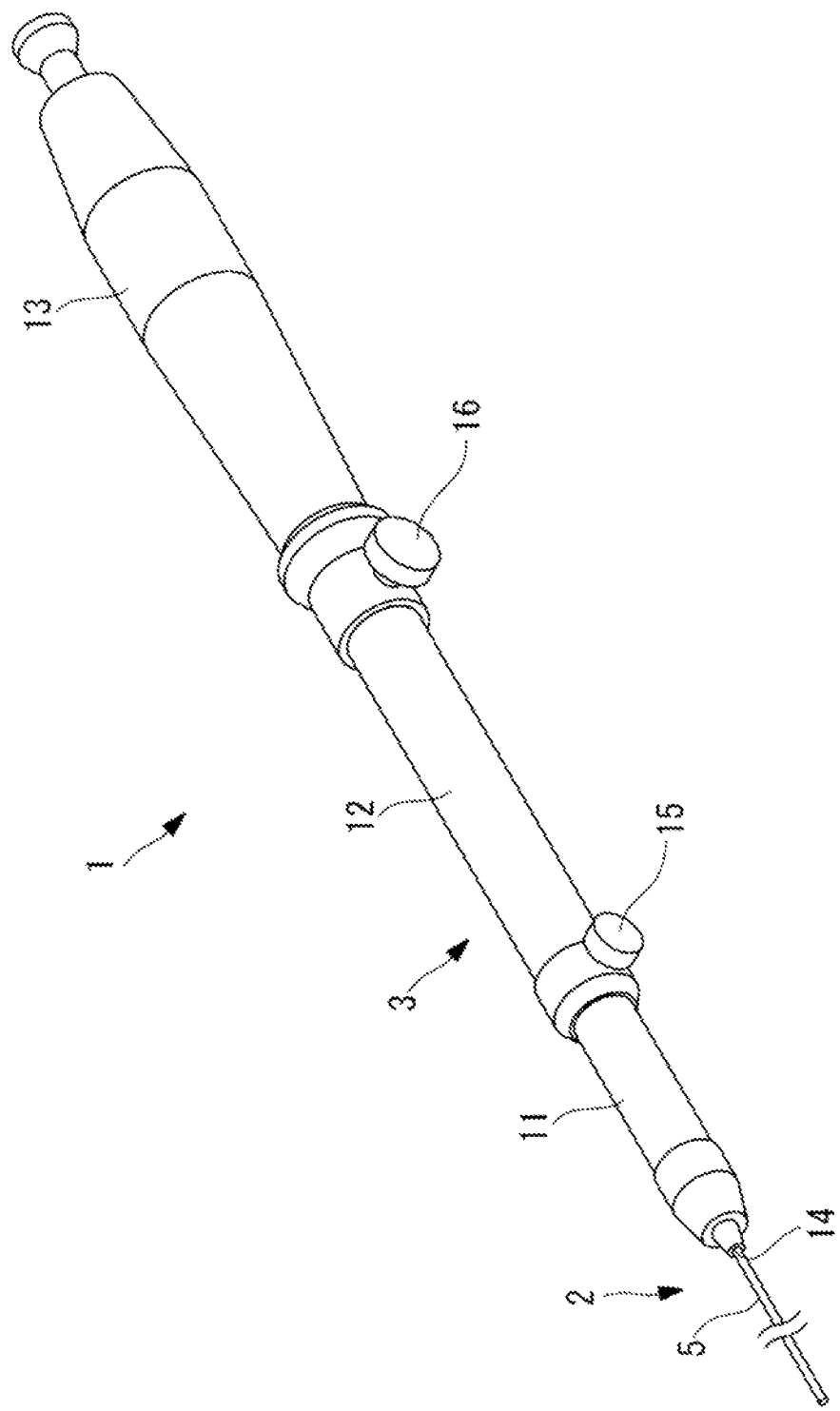
FIG. 2 is a perspective view illustrating the endoscopic puncture needle of FIG. 1.

As illustrated in FIG. 2, the endoscopic puncture needle 1 according to this embodiment includes an insertion body 2 to be inserted into the body, and a manipulation portion 3 for operating the insertion body 2.

The insertion body 2 is an elongated member, which can be inserted into the channel 110 from an opening thereof in the vicinity of the operation mechanism 109 of the ultrasonic endoscope 100 and is allowed to protrude from an opening in a vicinity of the ultrasonic transducer.

Figure 3:
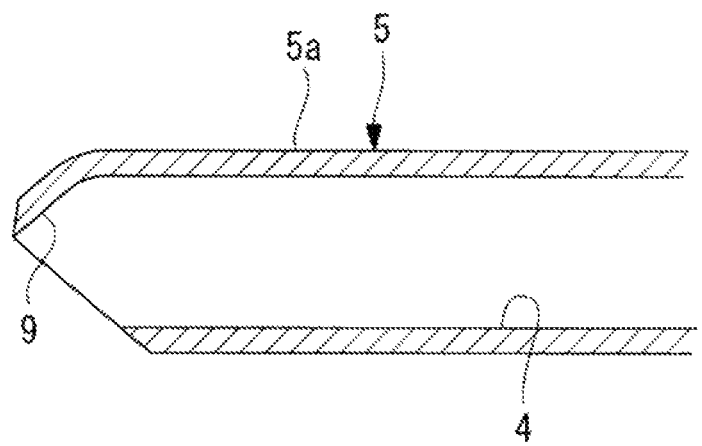
FIG. 3 is an enlarged vertical cross-sectional view fragmentarily illustrating an example of a distal end portion of a sheath to be included in the endoscopic puncture needle of FIG. 1.
Figure 4:
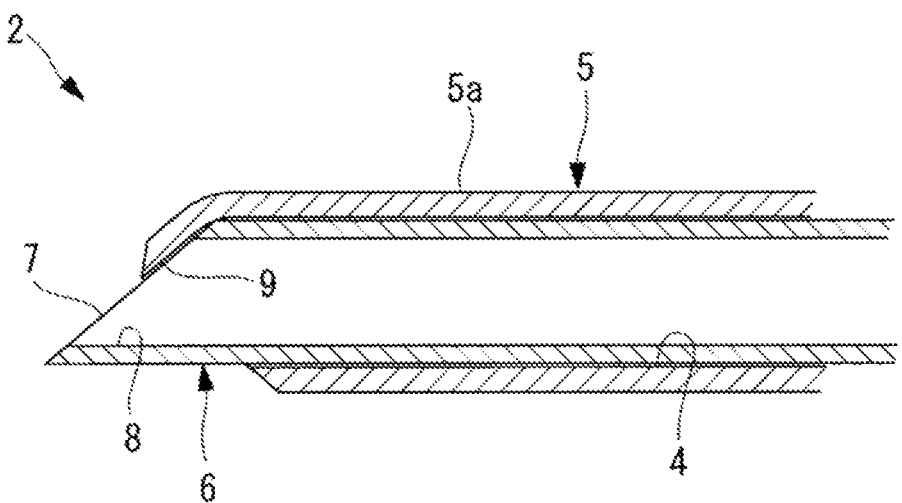
FIG. 4 is an enlarged vertical cross-sectional view illustrating a state in which a needle tube inserted in the sheath of FIG. 2 has come at a cutting-edge face thereof into abutment against an inclined surface.

As illustrated in FIGS. 3 and 4, the insertion body 2 includes a tubular sheath 5 and a needle tube 6. The tubular sheath 5 has a lumen 4 that extends in a longitudinal direction through the tubular sheath 5. The needle tube 6 is inserted movably in a longitudinal direction through the lumen 4 of the sheath 5.

The needle tube 6 is a tubular member having a circular cross-section. The tubular member has flexibility and elasticity sufficient to easily restore its linear form even when bent by an external force. As a material for the needle tube 6, for example, an alloy material such as a stainless alloy, a nickel-titanium alloy or a cobalt-chromium alloy can be adopted.

As illustrated in FIG. 4, the needle tube 6 includes, at a distal end thereof, a cutting-edge face 7 having a shape formed by cutting the needle tube 6 along a plane inclined in one direction relative to a longitudinal direction of the needle tube 6. The cutting-edge face 7 is configured pointed so that it comes into contact with a tissue and punctures the tissue with ease. A lumen 8 is disposed extending in a longitudinal direction through the needle tube 6, and opens at a location surrounded by the cutting-edge face 7. The opening of the lumen 8 has an elliptical shape.

The sheath 5 is a tubular member of a circular shape in cross-section, which has an inner diameter dimension slightly greater than an outer diameter of the needle tube 6 so that the needle tube 6 can be inserted movably in a longitudinal direction in the lumen 4. The sheath 5 is configured of resin, metal or the like.

In this embodiment, the sheath 5 has, as illustrated in FIG. 3, a shape formed at a distal end portion thereof by cutting it with a plane inclined in one direction relative to its longitudinal direction, and at a portion located in a circumferential direction on a most distal end thereof, also has a shape in which a sheath wall 5a includes on an inner surface side thereof an inclined surface 9 that is inclined inwards in a radial direction toward a distal end of the sheath 5.

As illustrated in FIG. 4, this inclined surface 9 is arranged at a location where the cutting-edge face 7 of the needle tube 6, which has been caused to advance in the lumen 4, comes into abutment on a proximal end side thereof against the inclined surface 9.

In other words, the sheath 5 and needle tube 6 are configured so that the needle tube 6 and the sheath 5 are integrally positioned with one another in a longitudinal direction at the location, where the cutting-edge face 7 of the needle tube 6 has come into abutment against the inclined surface 9 of the sheath 5, by causing the needle tube 6 to advance relative to the sheath 5 with the correlation in circumferential orientation between the sheath 5 and the needle tube 6 being set so that the direction of an inclination of the distal end of the sheath 5 and the direction of an inclination of the cutting-edge face 7 of the needle tube 6 become opposite to one another.

In this state, the cutting-edge face 7 of the needle tube 6 partially protrudes forward from the distal end of the sheath 5, and at this time, the inclined surface 9 assumes a position where the inclined surface 9 closes the distal end opening of the needle tube 6 to such an extent that the guide wire 10 (see FIG. 6B), which has been introduced into the lumen 8 of the needle tube 6, can protrudes forward from the distal end opening of the needle tube 6.

Further, an outer circumferential portion of the sheath wall 5a, which forms the inclined surface 9 of the sheath 5, has a shape formed by cutting off the sheath 5 so that the outer circumferential portion is tapered toward the distal end of the sheath 5. As a consequence, with the needle tube 6 inserted as illustrated in FIG. 4, formation of a large step by the sheath 5 relative to the cutting-edge face 7 is suppressed.

As illustrated in FIG. 2, the manipulation portion 3 includes an attachment adapter 11 formed of a cylindrical member for fixing the endoscopic puncture needle on the ultrasonic endoscope 100, a sheath slider 12 attached to a proximal end side of the attachment adapter 11, and a needle slider 13 disposed on a proximal end side of the sheath slider 12. The attachment adapter 11 and sheath slider 12 are configured, for example, of acrylonitrile butadiene styrene (ABS) resin or the like, and have an internal bore 14 through which the needle tube 6 and sheath 5 can be inserted along a longitudinal direction.

The attachment adapter 11 is inserted, on the proximal end side thereof, in the needle slider 12 formed in a tubular shape. The sheath slider 12 and the attachment adapter 11 are slidable relative to each other in the longitudinal direction, with their relative rotation about a longitudinal axis being suppressed, by engagement of one or more grooves or the like and one or more ridges or the like (not illustrated) formed in and on their outer and inner circumferential surfaces, respectively. The sheath slider 12 and the needle slider 13 are also configured similarly.

The sheath 5 disposed inside the sheath slider 12 is attached on the sheath slider 12.

On a distal end of the sheath slider 12, a fixing thumbscrew 15 is disposed. The fixing thumbscrew 15 manipulates movement of the sheath slider 12 in a longitudinal direction relative to the attachment adapter 11 when tightened, and allows such movement when loosened.

The needle tube 6 is attached at a proximal end portion thereof on the needle slider 13.

Figure 5A:
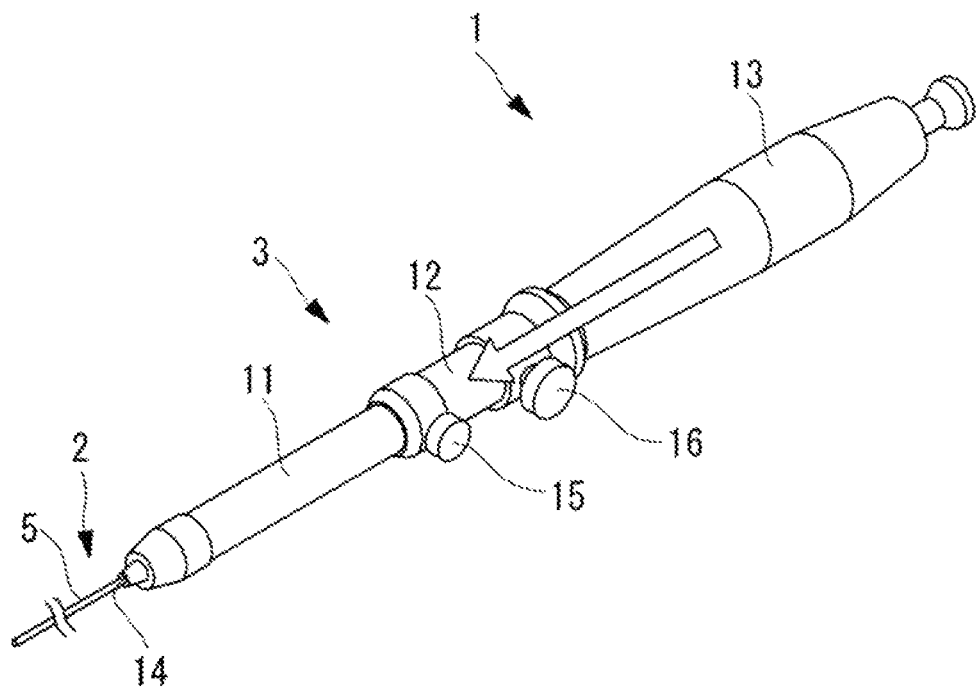
FIG. 5A is a perspective view explaining operation of a manipulation portion to achieve the state of FIG. 4.

Described specifically, the proximal end portion of the needle tube 6 protrudes from a proximal end of the sheath 5, extends into the needle slider 13, and is attached on the needle slider 13 at the proximal end portion of the needle slider 13. The needle slider 13 is connected to the sheath slider 12 so that the needle slider 13 is movable in a longitudinal direction relative to the sheath slider 12. As a consequence, the endoscopic puncture needle 1 is configured so that the needle tube 6 is caused to advance relative to the sheath 5 when the needle slider 13 is moved toward a distal end side of the endoscopic puncture needle 1 relative to the sheath slider 12 as illustrated in FIG. 5A.

On a distal end of the needle slider 13, a fixing thumbscrew 16 is disposed. The fixing thumbscrew 16 manipulates movement of the needle slider 13 relative to the sheath slider 12 when tightened, and allows such movement when loosened.

In this embodiment, the needle tube 6 and the sheath 5 are configured so that through abutment of a proximal end portion of the cutting-edge face 7 of the needle tube 6 against the inclined surface 9 at the proximal end of the sheath 5, the needle tube 6 is seized so as to prevent any further advance relative to the sheath 5.

Figure 5B:
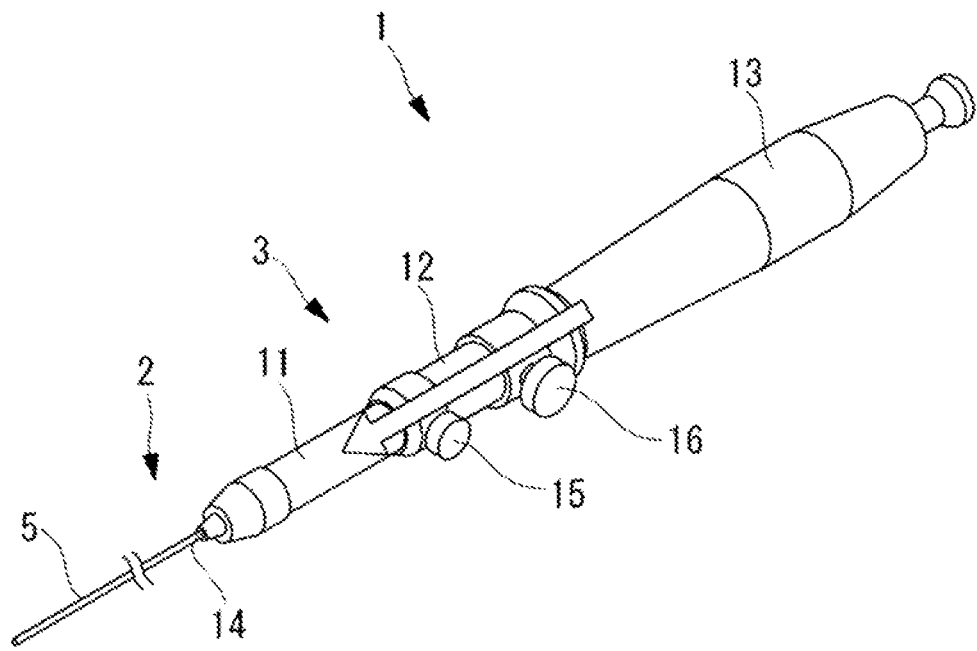
FIG. 5B is a perspective view explaining operation for causing the sheath and needle tube to advance from the state of FIG. 5A and to puncture.

The needle tube 6 and the sheath 5 are also configured so that, when the sheath slider 12 with the needle slider 13 fixed thereon by the fixing thumbscrew 16 is moved toward the distal end side of the endoscopic puncture needle 1 relative to the attachment adapter 11, the sheath 5 is caused to advance together with the needle tube 6 as illustrated in FIG. 5B.

Figure 5C:
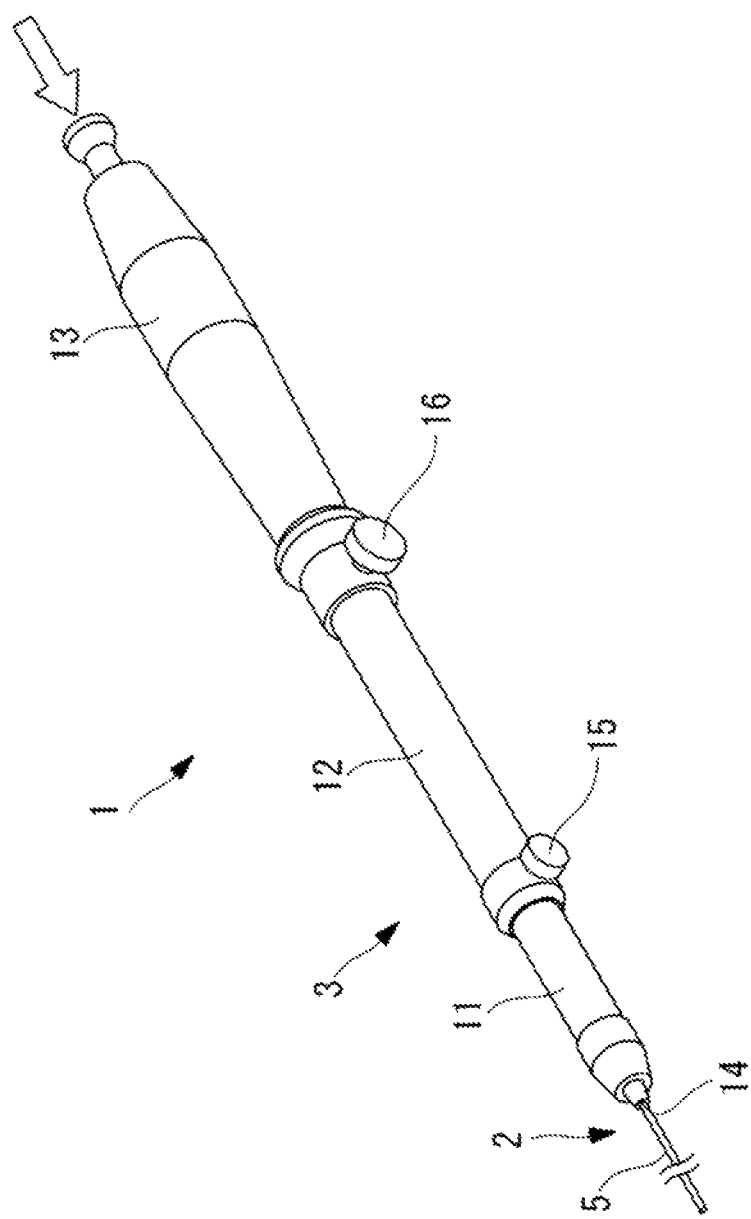
FIG. 5C is a perspective view explaining operation to introduce a guide wire in the state of FIG. 5B.

The needle tube 6 and the needle slider 13 are configured so that the needle tube 6 has a proximal end opening through a proximal end wall of the needle slider 13 and as illustrated in FIG. 5C, the guide wire 10 can be inserted into the lumen 8 of the needle tube 6 via the opening in the proximal end wall of the needle slider 13.

By moving the needle slider 13 toward a proximal end side of the endoscopic puncture needle 1 relative to the sheath slider 12, the cutting-edge face 7 at the distal end of the needle tube 6 can be received in the sheath 5. The endoscopic puncture needle 1 is now in an initial state before beginning its use.

A description will hereinafter be made about operation of the endoscopic puncture needle 1 of this embodiment configured as described hereinbefore.

In order to insert the guide wire 10 into a tubular tissue by using the endoscopic puncture needle 1 according to this embodiment, an operator inserts the insertion portion 101 of the ultrasonic endoscope 100 into the body, and introduces a distal end portion of the insertion portion 101 to a vicinity of a target tissue X while observing with the optical imaging system. After the introduction, the operator determines a site of puncture based on observation results by the optical imaging system and the ultrasonic probe 104.

Next, the operator inserts the insertion body 2 of the endoscopic puncture needle 1 from the distal end side thereof into the channel 110 through the opening in the vicinity of the operation mechanism 109 of the ultrasonic endoscope 100, and fixes the attachment adapter 11 in the vicinity of the operation mechanism 109. As a consequence, the endoscopic puncture needle 1 is attached on the ultrasonic endoscope 100 so that the endoscopic puncture needle 1 does not rotate relative to the operation mechanism 109.

By moving the sheath slider 12 in its longitudinal direction relative to the attachment adapter 11 while observing the sheath 5 and the inside of the body by the optical imaging system and the ultrasonic probe 104, the operator next adjusts the length of a protrusion of the sheath 5 from the distal end of the insertion portion 101 of the ultrasonic endoscope 100 to an appropriate extent so that the sheath 5 protrudes to a location where the sheath 5 can be identified by the optical imaging system.

Next, the fixing thumbscrew 16 is loosened from the initial state to move the needle slider 13 in its longitudinal direction relative to the sheath slider 12 so that the cutting-edge face 7 of the needle tube 6 is caused to advance to a location where the cutting-edge face 7 comes on the proximal end side thereof into abutment against the inclined surface 9 of the sheath 5. With the needle tube 6 advanced to the location of FIG. 4 relative to the sheath 5, the fixing thumbscrew 16 is tightened to fix the sheath 5 and the needle tube 6 so that they do not move with respect to one another.

Figure 6A:
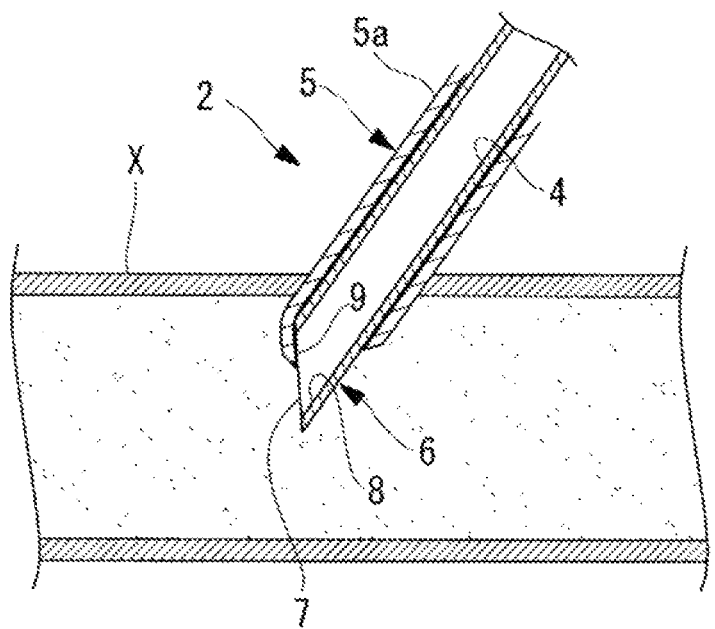
FIG. 6A is an enlarged vertical cross-sectional view illustrating a state in which the needle tube and sheath have punctured a wall of a tubular body tissue by the operation of FIG. 5B.

The sheath slider 12 is caused to advance again relative to the attachment adapter 11 in this state and at the same time, the sheath 5 and needle tube 6 are also caused to advance, whereby the target tissue X is punctured by the cutting-edge face 7 of the needle tube 6, the cutting-edge face 7 being exposed at the distal end of the sheath 5. As a consequence, the cutting-edge face 7 at the distal end of the needle tube 6 and a portion of the distal end portion of the sheath 5 are, as illustrated in FIG. 6A, inserted through a side wall of a tubular body tissue, for example, the bile duct as the target tissue X.

In this state, the operator inserts the guide wire 10 into the proximal end opening of the needle tube 6 in the proximal end wall of the needle slider 13. The guide wire 10 is caused to pass through the lumen 8 of the needle tube 6 and to protrude from the distal end opening of the needle tube 6, and is inserted into the body tissue X.

Figure 6B:
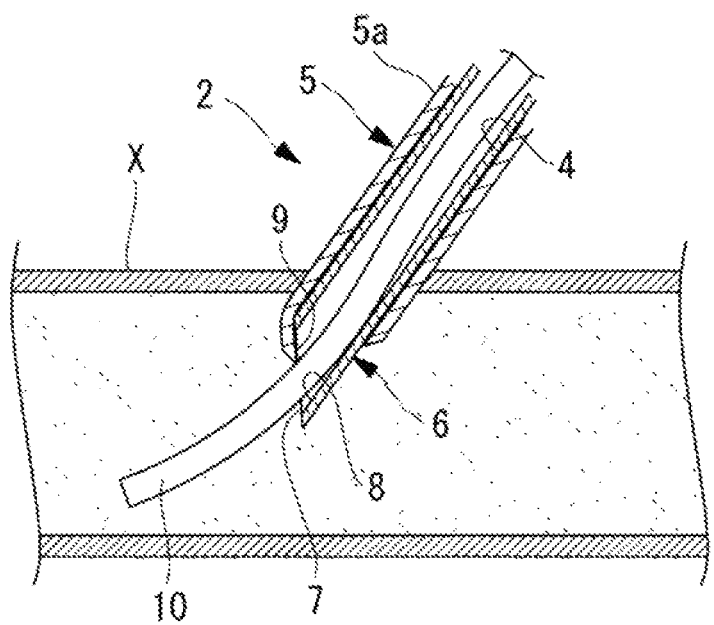
FIG. 6B is an enlarged vertical cross-sectional view illustrating a state in which the guide wire has been introduced by the operation of FIG. 5C.

In this case, the distal end of the needle tube 6 has the shape formed by cutting the needle tube 6 along the plane inclined relative to the longitudinal direction of the needle tube 6, and the distal end opening of the needle tube 6 opens diagonally forward. As illustrated in FIG. 6B, the guide wire 10 is therefore guided to pass between a proximal end opening of the sheath 5 and the needle tube 6 and then to extend in a direction that intersects a plane of the distal end opening of the needle tube 6.

Figure 6C:
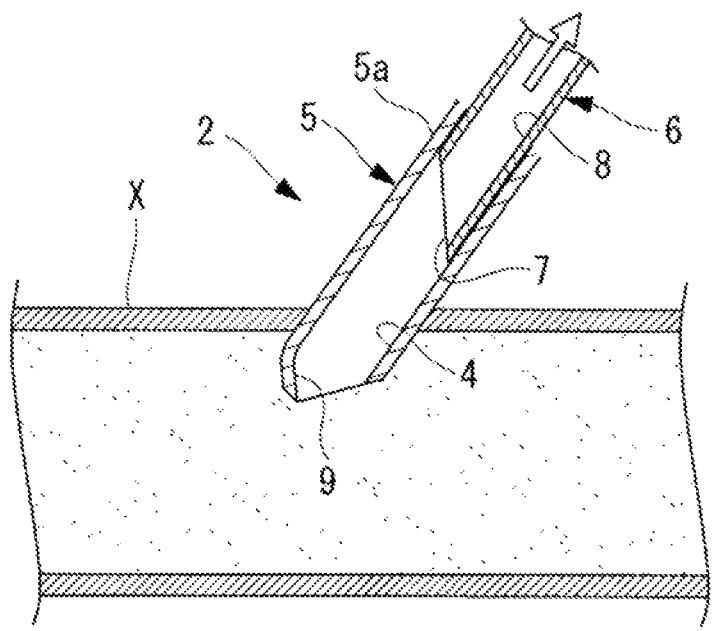
FIG. 6C is an enlarged vertical cross-sectional view illustrating a state in which the needle tube has been caused to retreat relative to the sheath from the state of FIG. 6B.

If the extending direction of the guide wire 10 is wrong at this time point, the fixing thumbscrew 16 is loosened with the guide wire 10 retreated once. As illustrated in FIG. 6C, the needle slider 13 is caused to retreat relative to the sheath slider 12 to withdraw the needle tube 6 alone while allowing the sheath 5 to still remain in the body tissue X. Subsequently, the guide wire 10 is caused to advance.

Figure 6D:
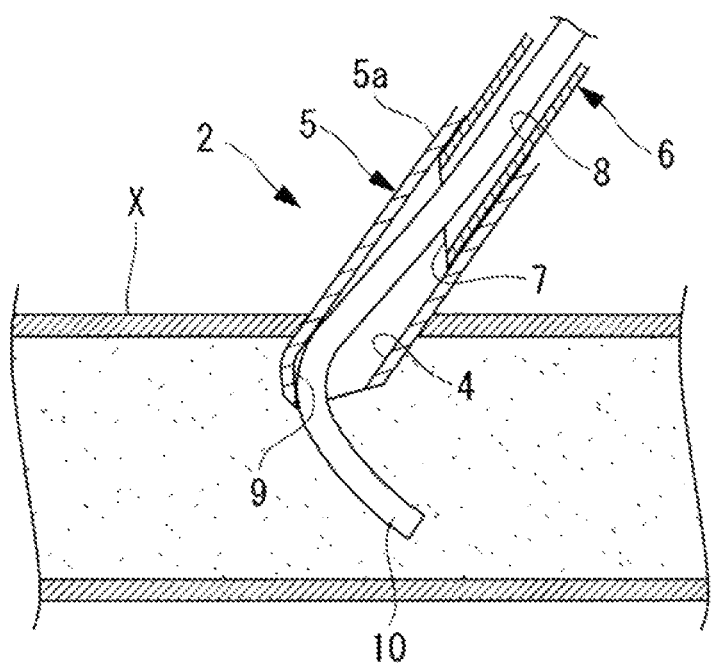
FIG. 6D is an enlarged vertical cross-sectional view illustrating a state in which the guide wire has been introduced in the state of FIG. 6C.

At the sheath 5 with the needle tube 6 withdrawn therefrom, the inclined surface 9 is disposed on the most distal end, and the distal end opening opens in a direction facing the inclined surface 9, in other words, in a direction opposite the direction in which the distal end opening of the needle tube 6 opens. Therefore, the guide wire 10 which has been caused to advance is guided by the inclined surface 9 and as illustrated in FIG. 6D, is guided to extend in an opposite direction toward the body tissue X.

According to the endoscopic puncture needle 1 of this embodiment, the extending direction of the guide wire 10 can be, as described hereinbefore, switched between the state, in which the cutting-edge face 7 of the needle tube 6 has been caused to protrude forward beyond the distal end of the sheath 5, and the state, in which the cutting-edge face 7 of the needle tube 6 has been caused to retreat toward a proximal end side of the sheath 5. As a consequence, there is a merit that the inserting direction of the guide wire 10 can be chosen after puncturing the needle tube 6 into the target tissue X.

Described specifically, the inserting direction of the guide wire 10 can be switched without performing the puncture of the target tissue X again with the needle tube 6, leading to a merit that the physical burden on the patient can be alleviated.

Figure 7:
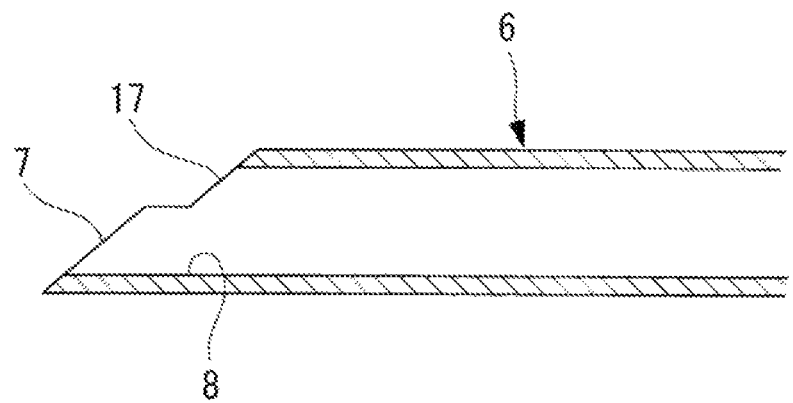
FIG. 7 is an enlarged view illustrating a modification of the shape of a distal end portion of the needle tube.
Figure 8:
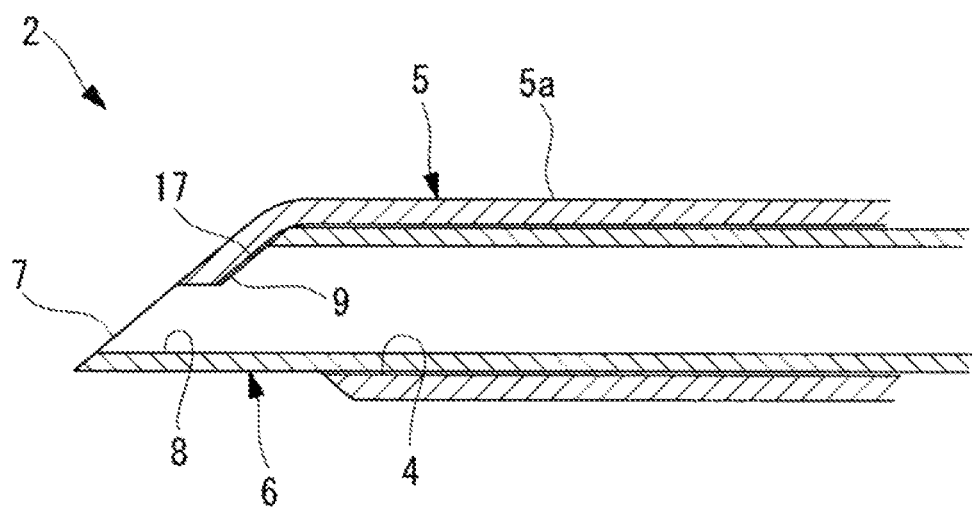
FIG. 8 is an enlarged vertical cross-sectional view illustrating a state in which the needle tube of FIG. 7 has come into abutment against the inclined surface of the sheath.

In this embodiment, a step 17, or stepped portion, may be included at the proximal end portion of the cutting-edge face 7 of the needle tube 6, where the cutting-edge face 7 comes into abutment against the inclined surface 9, as illustrated in FIG. 7. The step 17, or stepped portion, is recessed with a depth substantially equal to the thickness of the sheath wall 5a of the sheath 5. Reference is next made to FIG. 8, and the needle tube 6 is assumed to be caused to advance relative to the sheath 5 and to come into abutment against the inclined surface 9. If configured as described hereinbefore, the inclined surface 9 can be received in the step 17 to arrange the cutting-edge face 7 of the needle tube 6 substantially in flush with an outer circumferential surface of the sheath 5 so that the body tissue X can avoid being caught by the sheath 5 upon puncture. As a consequence, this configuration can facilitate the puncture work of the body tissue X by the needle tube 6 integrated with the sheath 5.

Figure 9:
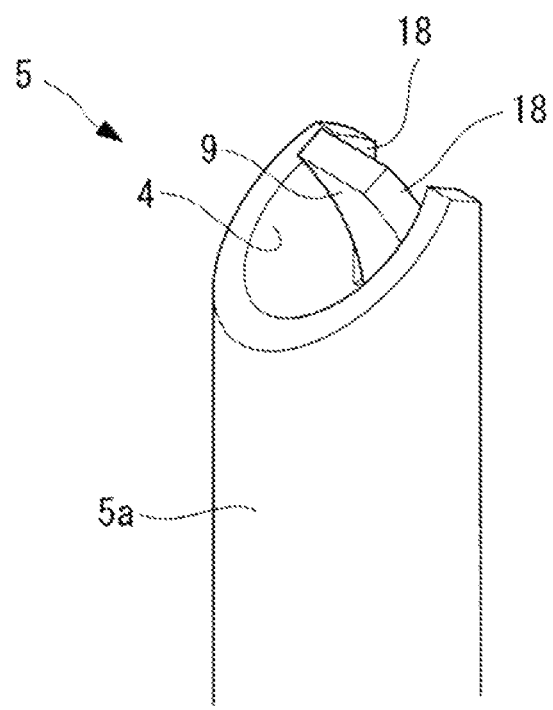
FIG. 9 is a fragmentary perspective view illustrating a modification of the sheath of FIG. 3.

In this embodiment, the sheath 5 may also be configured as illustrated in FIG. 9. Described specifically, slits 18 are formed extending in a longitudinal direction on circumferentially opposite sides of the sheath wall 5a that forms an inclined surface 9, whereby the sheath wall 5a that forms the inclined surface 9 is rendered deformable in a radial direction by elasticity.

Figure 10:
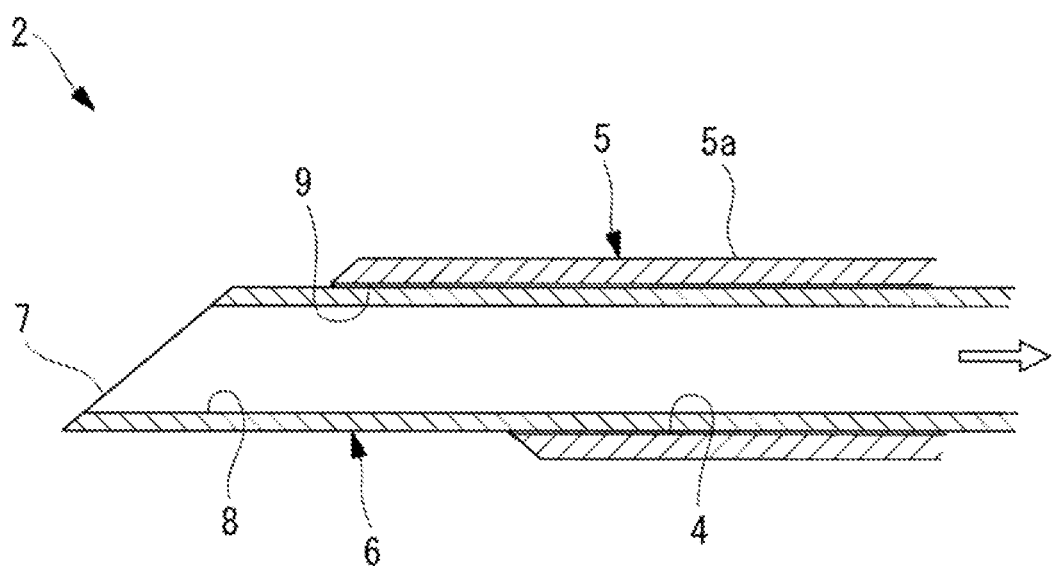
FIG. 10 is an enlarged vertical cross-sectional view illustrating a state in which the needle tube has been caused to advance through elastic deformation of a wall of the sheath of FIG. 9.

Reference is now had to FIG. 10. If configured as described hereinbefore, the sheath wall 5a that forms the inclined surface 9 can be elastically deformed to extend straight in a longitudinal direction by a push force which causes the needle tube 6 to advance relative to the sheath 5, and therefore the cutting-edge face 7 of the needle tube 6 can be caused to protrude forward in its entirety from the distal end of the sheath 5.

As a consequence, the body tissue X can be more easily punctured by the cutting-edge face 7 formed pointed. By introducing the guide wire 10 with the needle tube 6 protruding forward beyond the distal end of the sheath 5 as described hereinbefore, the guide wire 10 can be guided in the direction that intersects the plane of the distal end opening of the needle tube 6, as illustrated in FIG. 11.

Figure 11:
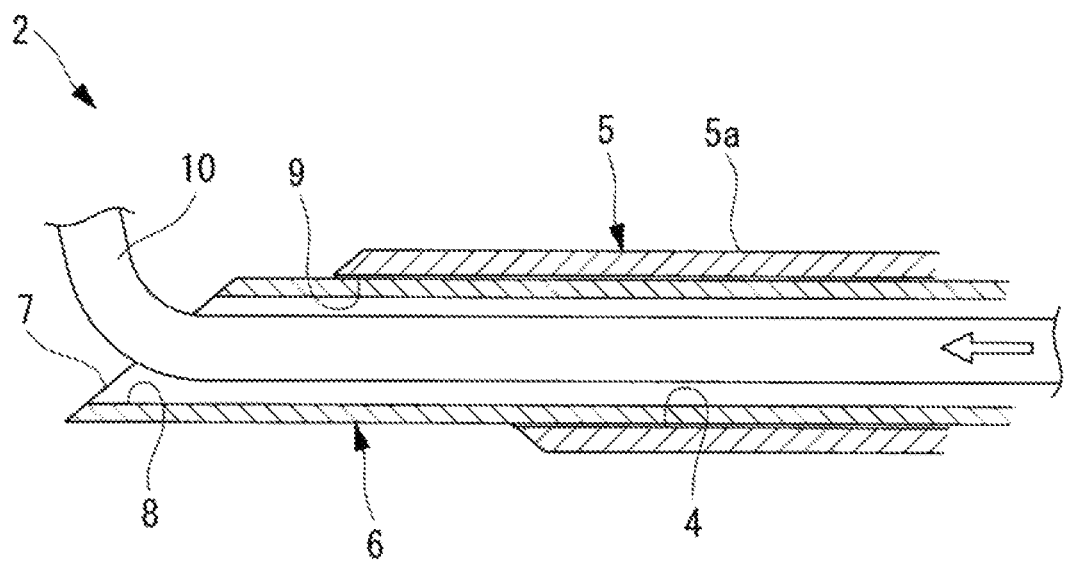
FIG. 11 is an enlarged vertical cross-sectional view illustrating a state in which the guide wire has been introduced in the state of FIG. 10.
Figure 12:
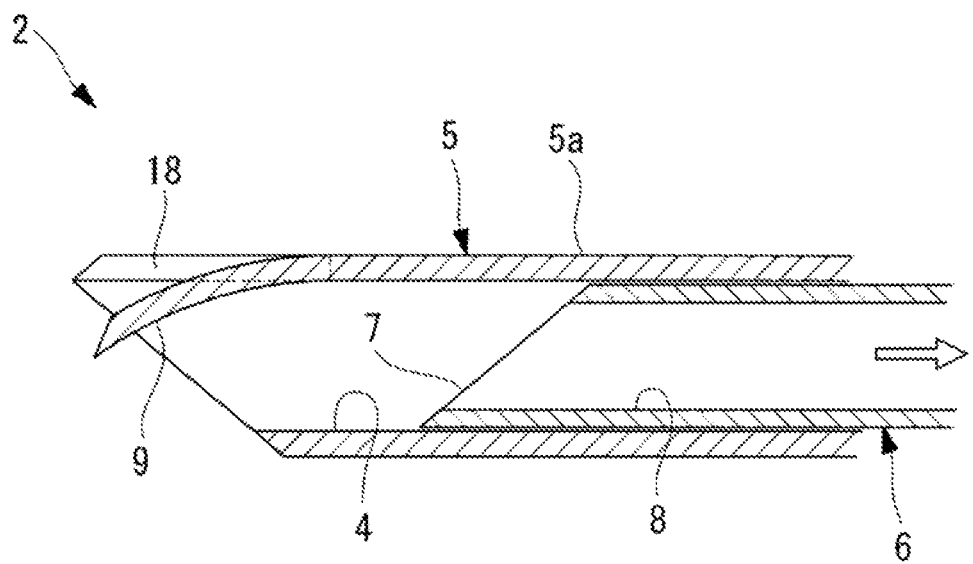
FIG. 12 is an enlarged vertical cross-sectional view illustrating a state in which the needle tube has been caused to retreat relative to the sheath from the state of FIG. 10.
Figure 13:
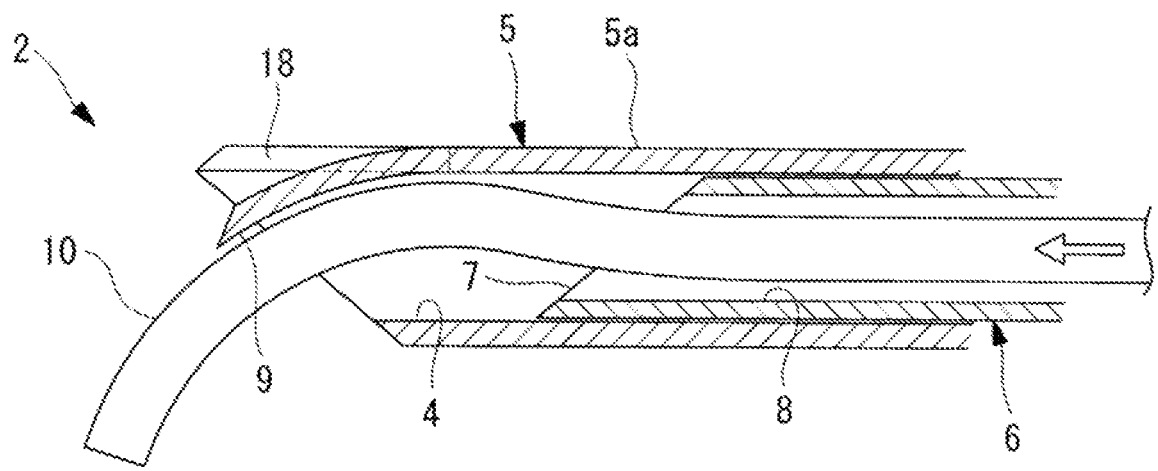
FIG. 13 is an enlarged vertical cross-sectional view illustrating a state in which the guide wire has been introduced in the state of FIG. 12.

If the introduction of the guide wire 10 in the direction illustrated in FIG. 11 is wrong, however, the needle tube 6 is caused to retreat toward the proximal end side of the sheath 5 relative to its distal end as illustrated in FIG. 12. In this state, the sheath wall 5a of the sheath 5, which corresponds to the inclined surface 9, restores radially inward to the original state by an elastic restoring force so that the inclined surface 9 is formed. As illustrated in FIG. 13, an introduction of the guide wire 10 in this state can guide the guide wire 10 in a direction different from that of FIG. 11.

Figure 14:
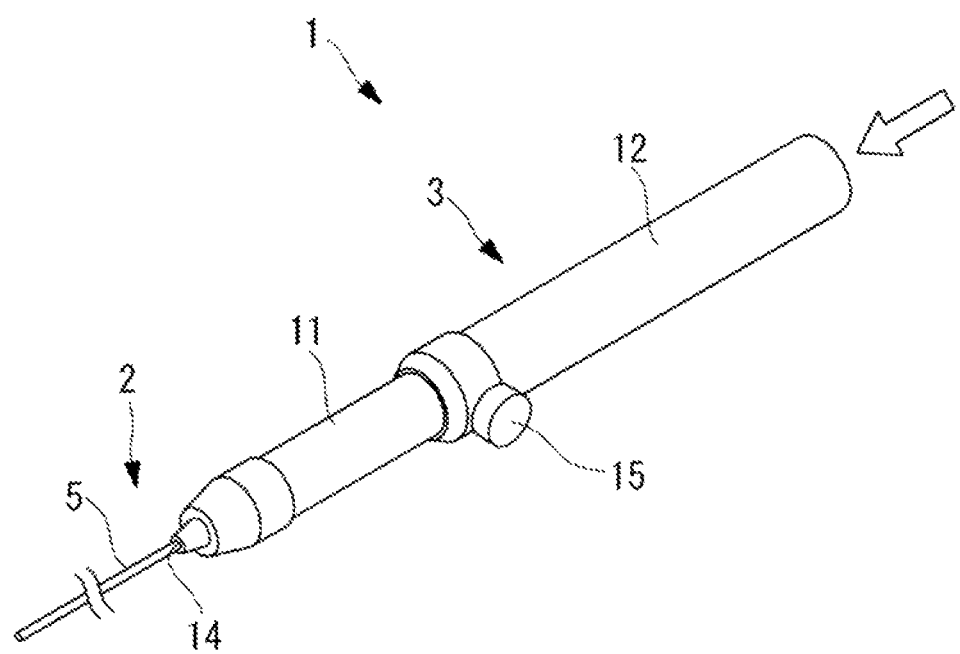
FIG. 14 is a perspective view illustrating a modification of FIG. 6C.

In this embodiment, the guide wire 10 is configured to be introduced with the needle tube 6 retreated toward the proximal end side of the sheath 5 relative to its distal end as illustrated in FIGS. 6C, 12 and 13. Instead of this configuration, another configuration may be adopted. As illustrated in FIG. 14, with the needle slider 13 cause to significantly retreat relative to the sheath slider 12 so that the needle tube 6 has been completely withdrawn out of the sheath 5, the guide wire 10 may be introduced from a proximal end opening of the sheath 5, which opens in a proximal end wall of the sheath slider 12.

Figure 15:
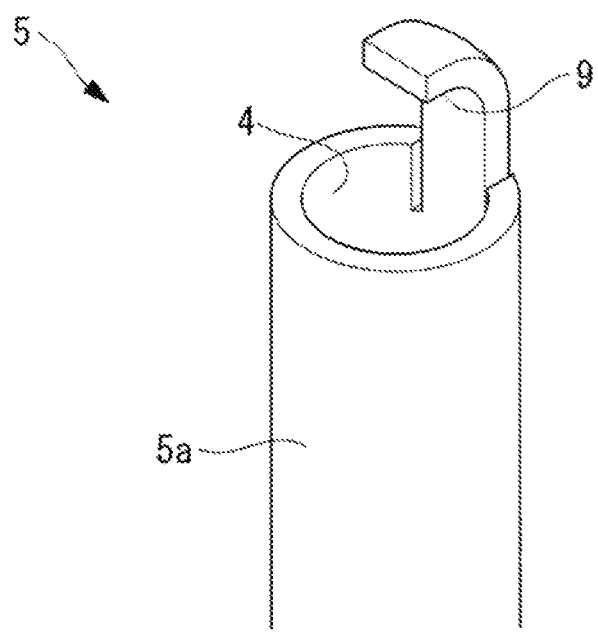
FIG. 15 is a fragmentary perspective view illustrating a modification of FIG. 9.

In this embodiment, the distal end of the sheath 5 is in the shape formed by cutting it with the plane inclined relative to the longitudinal direction. However, the distal end of the sheath 5 should not be limited to this shape and as illustrated in FIG. 15, only a portion in a circumferential direction of the sheath wall 5a, the portion forming an inclined surface 9, may be configured to protrude forward beyond the remaining portion thereof. As a consequence, the inclined surface 9 is also disposed forward of the lumen 4 of the sheath 5 so that the guide wire 10, which has been introduced through the lumen 4, can be guided in one direction along the inclined surface 9.

In this embodiment, the endoscopic puncture needle 1 to be used attached to the ultrasonic endoscope 100 is exemplified. Instead of such an ultrasonic endoscope, the endoscopic puncture needle 1 may also be used attached to any other desired endoscopes.

In this embodiment, as the cutting-edge face 7 of the needle tube 6, one formed by cutting the distal end of the needle tube 6 with the plane inclined in one direction relative to the longitudinal direction is adopted. Instead of such a cutting-edge face, a cutting-edge face of a different shape may be adopted insofar as it is inclined relative to the longitudinal direction of the needle tube 6, for example, a cutting-edge face configured by forming the distal end of the needle tube 6 in a conical or polygonal pyramid shape or a cutting-edge face inclined on a side thereof relative to the longitudinal direction and inclined on an opposite side thereof at an angle different from that on the former side relative to the longitudinal direction.

In sum, one aspect of the disclosed technology is directed to a puncture needle access system for introducing guide wire into an interior of a tubular organ. The success system includes an endoscope having an insertion portion. An endoscopic puncture needle is configured to be engaged with the insertion portion. The endoscopic puncture needle includes an elongated tubular sheath having a lumen that extends in a longitudinal direction through the elongated tubular sheath. A tubular needle tube is inserted movably in the longitudinal direction into the lumen of the elongated tubular sheath. The tubular needle tube includes an inclined cutting-edge face formed at a distal end thereof relative to the longitudinal direction. The elongated tubular sheath includes an inclined surface oriented toward a distal end of the sheath so that the inclined surface comes closer to a central axis of the elongated tubular sheath. The distal end of the sheath on a side facing the inclined surface with the lumen interposed in a radial direction therebetween is located on a proximal end side of the sheath relative to a distal end of the inclined surface.

The inclined surface is formed at a portion in a circumferential direction of an inner surface of the lumen at a distal end portion of the elongated tubular sheath and is disposed at a location where, with the tubular needle tube inserted in the lumen protruding forward at a distal end of the cutting-edge face from the distal end of the elongated tubular sheath. The cutting-edge face comes into abutment on a proximal end side thereof against the inclined surface. A guide wire is inserted in the tubular needle tube can protrude from a distal end of the needle tube. The inclined surface is configured of an inner surface of a wall of the elongated tubular sheath. The inner surface has been formed by bending a portion in a circumferential direction of the distal end portion of the elongated tubular sheath inward in a radial direction.

The cutting-edge face of the tubular needle tube includes a stepped portion recessed from the cutting-edge face with a depth dimension substantially equal to a thickness dimension of the wall of the elongated tubular sheath. The stepped portion is configured to come into abutment against the inclined surface with the distal end of the cutting-edge face of the tubular needle tube being caused to protrude forward from the distal end of the sheath. The wall of the portion of the elongated tubular sheath, the portion forming the inclined surface, is configured to be elastically deformable to a location where the wall becomes substantially parallel to the longitudinal direction of the elongated tubular sheath by pressing the inclined surface in the longitudinal direction of the elongated tubular sheath with the tubular needle tube brought into abutment against the inclined surface.

Another aspect of the disclosed technology is directed to an endoscopic puncture needle used in an endoscope having an insertion portion. The endoscopic puncture needle includes an elongated open ended tubular sheath. A tubular needle tube is configured to be inserted movably in a longitudinal direction into the elongated open ended tubular sheath. The tubular needle tube includes an inclined cutting-edge face formed at a distal end thereof relative to the longitudinal direction. The elongated open ended tubular sheath includes an inclined surface oriented toward a distal end of the sheath so that the inclined surface comes closer to a central axis of the elongated tubular sheath. And the distal end of the sheath on a side facing the inclined surface interposed in a radial direction therebetween is located on a proximal end side of the sheath relative to a distal end of the inclined surface.

The inclined surface is formed at a portion in a circumferential direction of an inner surface of the lumen at a distal end portion of the elongated tubular sheath and is disposed at a location where, with the tubular needle tube is inserted in the lumen protruding forward at a distal end of the cutting-edge face from the distal end of the elongated tubular sheath. The cutting-edge face comes into abutment on a proximal end side thereof against the inclined surface, and a guide wire is inserted in the tubular needle tube can protrude from a distal end of the needle tube. The inclined surface is configured of an inner surface of a wall of the elongated tubular sheath, and the inner surface has been formed by bending a portion in a circumferential direction of the distal end portion of the elongated tubular sheath inward in a radial direction.

The cutting-edge face of the tubular needle tube includes a stepped portion recessed from the cutting-edge face with a depth dimension substantially equal to a thickness dimension of the wall of the elongated tubular sheath. And the stepped portion is configured to come into abutment against the inclined surface with the distal end of the cutting-edge face of the tubular needle tube being caused to protrude forward from the distal end of the sheath. The wall of the portion of the elongated tubular sheath, the portion forming the inclined surface, is configured to be elastically deformable to a location where the wall becomes substantially parallel to the longitudinal direction of the elongated tubular sheath by pressing the inclined surface in the longitudinal direction of the elongated tubular sheath with the tubular needle tube brought into abutment against the inclined surface.

A further aspect of the disclosed technology is directed to a method of introducing a guide wire into an interior of a tubular organ. The method comprising: inserting an insertion portion of an endoscope into a body; guiding a needle tube and a sheath to advance relative to the insertion portion introduced in the body, whereby the needle tube and sheath are caused to puncture a tubular wall of the tubular organ; retreating the needle tube toward a proximal end side relative to the sheath with the sheath still remaining at a distal end thereof in the interior of the tubular organ; and inserting the guide wire to extend from the distal end of the sheath into the interior of the tubular organ with the needle tube being located at a proximal end side thereof on a distal end relative to the proximal end of the sheath.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A puncture needle access system for introducing a guide wire into an interior of a tubular organ comprising:
   an endoscope including an insertion portion; and
   an endoscopic puncture needle configured to be engaged with the insertion portion, the endoscopic puncture needle including:
      an elongated tubular sheath including a lumen that extends in a longitudinal direction through the elongated tubular sheath; and
      a tubular needle tube configured to be inserted movably in the longitudinal direction into the lumen of the elongated tubular sheath,
   wherein:
      the tubular needle tube includes an inclined cutting-edge face formed at a distal end thereof relative to the longitudinal direction,
      the elongated tubular sheath includes an inclined surface extending in a distal direction along the longitudinal direction so as to be inclined toward a central axis of the elongated tubular sheath,
      a distal end of the inclined surface is positioned on a distal end side of a distal end of a radially opposite side of the elongated tubular sheath that faces the inclined surface with the lumen interposed in a radial direction therebetween, and
      the tubular needle tube is configured to be advanced distally along the longitudinal direction in the lumen of the elongated tubular sheath such that a proximal end side of the cutting-edge face of the tubular needle tube abuts against the inclined surface of the elongated tubular sheath and a distal end side of the cutting-edge face protrudes distally beyond the distal end of the elongated tubular sheath.

2. The puncture needle access system of claim 1, wherein the inclined surface is a portion of an inner circumferential surface of a distal end portion of the elongated tubular sheath and is disposed such that the guide wire inserted in the tubular needle tube can protrude from a distal end of the needle tube in a state in which the tubular needle tube is inserted into the lumen such that the proximal end side of the cutting-edge face of the tubular needle tube abuts against the inclined surface of the elongated tubular sheath and the distal end side of the cutting-edge face protrudes distally beyond the distal end of the elongated tubular sheath.

3. The puncture needle access system according to claim 2, wherein the tubular needle tube is movable between:
   (i) the state in which the tubular needle tube is inserted into the lumen such that the proximal end side of the cutting-edge face abuts against the inclined surface of the elongated tubular sheath and the distal end side of the cutting-edge face protrudes distally beyond the distal end of the elongated tubular sheath, and
   (ii) a different state in which the tubular needle tube is inserted into the lumen such that the proximal end side of the cutting-edge face is spaced away from the inclined surface of the elongated tubular sheath and the distal end side of the cutting-edge face is disposed inside the lumen of the elongated tubular sheath.

4. The puncture needle access system according to claim 3, wherein in the different state, the guide wire inserted in the tubular needle tube protrudes from the distal end of the elongated tubular sheath while contacting the inclined surface of the elongated tubular sheath.

5. The puncture needle access system of claim 1, wherein the inclined surface is an inner surface of a bent portion of a circumferential wall of the elongated tubular sheath at a distal end side thereof that has been bent inward in the radial direction.

6. The puncture needle access system of claim 5, wherein the bent portion of the circumferential wall of the elongated tubular sheath is configured to be elastically deformed to a state where the bent portion extends substantially parallel to the longitudinal direction of the elongated tubular sheath when the tubular needle tube is advanced distally in the lumen such that the proximal end side of the cutting-edge face abuts against the inclined surface and presses the inclined surface in the longitudinal direction.

7. The puncture needle access system of claim 1, wherein:
the cutting-edge face of the tubular needle tube includes a stepped portion recessed from the cutting-edge face with a depth dimension substantially equal to a thickness dimension of a wall of the elongated tubular sheath, and
the stepped portion is configured to abut against the inclined surface with the distal end side of the cutting-edge face of the tubular needle tube protruding distally from the distal end of the elongated tubular sheath when the tubular needle tube is advanced distally along the longitudinal direction in the lumen of the elongated tubular sheath.

8. The puncture needle access system according to claim 1, wherein a distal end opening of the elongated tubular sheath is inclined with respect to the radial direction of the elongated tubular sheath, and the distal end opening of the elongated tubular sheath faces in a different direction than a distal end opening of the tubular needle tube.

9. An endoscopic puncture needle comprising:
an elongated open ended tubular sheath; and
a tubular needle tube configured to be inserted movably in a longitudinal direction into the elongated open ended tubular sheath,
wherein:
the tubular needle tube includes an inclined cutting-edge face formed at a distal end thereof relative to the longitudinal direction,
the elongated open ended tubular sheath includes an inclined surface that extends in a distal direction along the longitudinal direction so as to be inclined toward a central axis of the elongated open ended tubular sheath,
a distal end of the inclined surface is positioned on a distal end side of a distal end of a radially opposite side of the elongated open ended tubular sheath that faces the inclined surface with the central axis interposed in a radial direction therebetween, and
the tubular needle tube is configured to be advanced distally along the longitudinal direction in the elongated open ended tubular sheath such that a proximal end side of the cutting-edge face of the tubular needle tube abuts against the inclined surface of the elongated open ended tubular sheath and a distal end side of the cutting-edge face protrudes distally beyond the distal end of the elongated open ended tubular sheath.

10. The endoscopic puncture needle of claim 9, wherein the inclined surface is a portion of an inner circumferential surface of a distal end portion of the elongated open ended tubular sheath and is disposed such that a guide wire inserted in the tubular needle tube can protrude from a distal end of the needle tube in a state in which the tubular needle tube is inserted into the elongated open ended tubular sheath such that the proximal end side of the cutting-edge face of the tubular needle tube abuts against the inclined surface of the elongated open ended tubular sheath and the distal end side of the cutting-edge face protrudes distally beyond the distal end of the elongated open ended tubular sheath.

11. The endoscopic puncture needle according to claim 10, wherein the tubular needle tube is movable between:
(i) the state in which the tubular needle tube is inserted into the elongated open ended tubular sheath such that the proximal end side of the cutting-edge face abuts against the inclined surface of the elongated open ended tubular sheath and the distal end side of the cutting-edge face protrudes distally beyond the distal end of the elongated open ended tubular sheath, and
(ii) a different state in which the tubular needle tube is inserted into the elongated open ended tubular sheath such that the proximal end side of the cutting-edge face is spaced away from the inclined surface of the elongated open ended tubular sheath and the distal end side of the cutting-edge face is disposed inside the elongated open ended tubular sheath.

12. The endoscopic puncture needle according to claim 11, wherein in the different state, the guide wire inserted in the tubular needle tube protrudes from the distal end of the elongated open ended tubular sheath while contacting the inclined surface of the elongated open ended tubular sheath.

13. The endoscopic puncture needle of claim 9, wherein the inclined surface is an inner surface of a bent portion of a circumferential wall of the elongated open ended tubular sheath at a distal end side thereof that has been bent inward in the radial direction.

14. The endoscopic puncture needle of claim 13, wherein the bent portion of the circumferential wall of the elongated open ended tubular sheath is configured to be elastically deformed to a state where the bent portion extends substantially parallel to the longitudinal direction of the elongated open ended tubular sheath when the tubular needle tube is advanced distally in the elongated open ended tubular sheath such that the proximal end side of the cutting-edge face abuts against the inclined surface and presses the inclined surface in the longitudinal direction.

15. The endoscopic puncture needle of claim 9, wherein:
the cutting-edge face of the tubular needle tube includes a stepped portion recessed from the cutting-edge face with a depth dimension substantially equal to a thickness dimension of a wall of the elongated tubular sheath, and
the stepped portion is configured abut against the inclined surface with the distal end side of the cutting-edge face of the tubular needle tube protruding distally from the distal end of the elongated open ended tubular sheath when the tubular needle tube is advanced distally along the longitudinal direction in the elongated open ended tubular sheath.

16. The endoscopic puncture needle according to claim 9, wherein a distal end opening of the elongated open ended tubular sheath is inclined with respect to the radial direction of the elongated open ended tubular sheath, and the distal end opening of the elongated open ended tubular sheath faces in a different direction than a distal end opening of the tubular needle tube.

\* \* \* \* \*